US012690937B2

(12) United States Patent
Bass et al.

(10) Patent No.: US 12,690,937 B2
(45) **Date of Patent: *Jul. 28, 2026**

(54) OPTICAL FIBER HAVING AN EXPANDED LIGHT PATTERN

(71) Applicant: KATALYST SURGICAL, LLC, Chesterfield, MO (US)

(72) Inventors: Eric Bass, St. Louis, MO (US); Anthony Kiel, Troy, MP (US)

(73) Assignee: KATALYST SURGICAL, LLC, Chesterfield, MO (US)

( * ) Notice: Subject to any disclaimer, the term of this patent is extended or adjusted under 35 U.S.C. 154(b) by 279 days.

This patent is subject to a terminal disclaimer.

(21) Appl. No.: 18/571,828

(22) PCT Filed: Jun. 22, 2022

(86) PCT No.: PCT/US2022/034615

§ 371 (c)(1),
(2) Date: Dec. 19, 2023

(87) PCT Pub. No.: WO2022/271888

PCT Pub. Date: Dec. 29, 2022

(65) Prior Publication Data

US 2024/0288619 A1 Aug. 29, 2024

Related U.S. Application Data

(60) Provisional application No. 63/214,139, filed on Jun. 23, 2021.

(51) Int. Cl.
A61B 90/30 (2016.01)
A61F 9/007 (2006.01)
(Continued)

(52) U.S. Cl.
CPC ............ A61B 90/30 (2016.02); G02B 6/0006 (2013.01); G02B 6/0008 (2013.01);
(Continued)

(58) Field of Classification Search
CPC .............. A61B 90/30; A61B 2090/306; A61B 2090/309; A61F 9/007; G02B 6/0006;
(Continued)

(56) References Cited

U.S. PATENT DOCUMENTS

| | | | | |
|---|---|---|---|---|
| 6,324,326 B1 * | 11/2001 | Dejneka | ............... | G02B 6/1228 |
| | | | | 359/341.1 |
| 7,470,269 B2 * | 12/2008 | Auld | ...................... | A61B 90/36 |
| | | | | 606/4 |

(Continued)

OTHER PUBLICATIONS

Haynes Dionne M et al, "Optical fibre tapers: focal reduction and magnification", Proceedings of SPIE, IEEE, US,vol. 8450, Sep. 13, 2012 (Sep. 13, 2012), p. 84503J-84503J, XP060028611.

*Primary Examiner* — Ryan A Lepisto
(74) *Attorney, Agent, or Firm* — NIXON PEABODY LLP; Jeffrey L. Costellia

(57) ABSTRACT

An optical fiber (170) for transmitting a light beam by a light source including a proximal portion (172) configured to receive the light beam from the light source (122), the proximal portion having a first numerical aperture, a distal portion (174) configured to emit the light beam to illuminate a surgical field (180), the distal portion having a second numerical aperture, and a central portion (176) extending between the proximal portion and the distal portion, the central portion having a third numerical aperture, The optical fiber is configured to receive the light beam at the proximal portion at the first numerical aperture and output the light beam from the distal portion at the second numerical aperture, wherein the second numerical aperture is greater than the first numerical aperture.

18 Claims, 7 Drawing Sheets

(51) Int. Cl.

| | |
|---|---|
| *F21V 8/00* | (2006.01) |
| *G02B 6/122* | (2006.01) |
| *G02B 23/24* | (2006.01) |
| *G02B 27/48* | (2006.01) |

(52) U.S. Cl.
CPC ....... *G02B 6/1228* (2013.01); *G02B 23/2469* (2013.01); *G02B 27/48* (2013.01); *A61B 2090/306* (2016.02); *A61B 2090/309* (2016.02); *A61F 9/007* (2013.01)

(58) Field of Classification Search
CPC ................ G02B 6/0008; G02B 6/1228; G02B 23/2469; G02B 27/48
See application file for complete search history.

(56) References Cited

U.S. PATENT DOCUMENTS

| | | | | |
|---|---|---|---|---|
| 7,731,710 | B2 * | 6/2010 | Smith | A61F 9/007 362/558 |
| 7,761,139 | B2 * | 7/2010 | Teamney | A61B 5/6848 600/476 |
| 8,767,783 | B2 * | 7/2014 | Kusukame | G02B 27/48 372/27 |
| 9,055,885 | B2 * | 6/2015 | Horvath | A61B 3/0008 |
| 9,060,841 | B2 * | 6/2015 | McCawley | A61F 9/00763 |
| 9,072,587 | B2 * | 7/2015 | Smith | A61F 9/007 |
| 10,441,157 | B2 * | 10/2019 | Smith | G02B 6/0008 |
| 12,222,564 | B2 * | 2/2025 | Griffin | G02B 6/4206 |
| 12,372,730 | B2 * | 7/2025 | Griffin | G02B 6/4203 |
| 12,455,413 | B2 * | 10/2025 | Schultheis | G02B 23/26 |
| 2006/0184162 | A1 * | 8/2006 | Smith | A61B 3/0008 606/4 |
| 2007/0179430 | A1 * | 8/2007 | Smith | A61F 9/00736 604/20 |
| 2017/0156581 | A1 * | 6/2017 | Smith | G02B 6/0006 |

* cited by examiner

OPTICAL FIBER HAVING AN EXPANDED LIGHT PATTERN

CROSS REFERENCE TO RELATED APPLICATIONS

The present application is a National Stage of International Application No. PCT/US2022/034615, filed 22 Jun. 2022, which claims priority to U.S. Provisional Application No. 63/214,139 filed Jun. 23, 2021 entitled OPTICAL FIBER HAVING AN EXPANDED LIGHT PATTERN and which is incorporated herein by reference.

BACKGROUND ART

The subject matter herein relates generally to an optical fiber having an expanded light pattern, and in particular an optical fiber to provide illumination to a surgical site during an ophthalmic surgical procedure.

Various ophthalmic surgical procedures, sometimes referred to as vitreo-retinal procedures, are commonly performed in the posterior segment of the eye. Ophthalmic surgical procedures are appropriate to treat many serious conditions of the posterior segment, such as age-related macular degeneration (AMD), diabetic retinopathy and diabetic vitreous hemorrhage, macular hole, retinal detachment, epiretinal membrane, CMV retinitis, and many other ophthalmic conditions. During the surgical procedures, proper illumination of the inside of the eye is important. Typically, ophthalmic illumination devices, such as endoilluminator systems can provide light for the surgical site. A user, such as a surgeon or other medical professional, can insert the device into the eye to illuminate the inside of the eye. A light source and other illumination optics direct a light beam through an optical fiber of the illumination device. It is desirable to provide an expanded or wide-angle illumination field to illuminate as large a portion of the inside of the eye as possible. However, the miniaturization of ophthalmic surgery instruments that provide illumination to a surgical site has limited the capability of the optical fiber to introduce enough light and/or at a wide enough angle to the surgical site for effective visualization by the surgeon.

It is desirable to minimize the number and size of incisions required to perform ophthalmic surgical procedures. Typically, incisions are only made large enough to accommodate the size of the microsurgical instrument being inserted into the interior of the eye. Therefore, minimizing the size of the microsurgical instrument can minimize the incision size. Reducing the number of incisions may be accomplished by integrating various microsurgical instruments. For example, the optical fiber may be incorporated into the working end of a microsurgical instrument to eliminate the need for a separate illumination incision.

However, prior attempts at integrating multiple microsurgical instruments resulted in larger instruments requiring larger incisions or were accompanied by a corresponding decrease in the performance of one or both of the integrated surgical instruments. For example, the size of the optical fiber used in microsurgical instruments has been limited by the size of the light beam emitted by conventional light sources that use conventional light elements, such as Tungsten, Halogen, incandescent, Metal Halide arc, Xenon arc, Mercury Vapor arc, and LED.

All of the incandescent and arc sources within these lamps are large relative to the size of the fibers that they coupled with. Generally, conventional light sources are limited to use with optical fibers with a diameter of 250 microns or greater.

These conventional light sources are not capable of emitting a light beam with a focal point that is smaller than an opening aperture of the optical fiber. As a result, reducing the size of the optical fiber would reduce the amount of light transmitted by the optical fiber to an unacceptable level of performance.

Accordingly, there is a need for an ophthalmic illumination device having an optical fiber that provides an expanded light pattern for illuminating a surgical site during an ophthalmic surgical procedure.

DETAILED DESCRIPTION OF THE INVENTION

Figure 1:
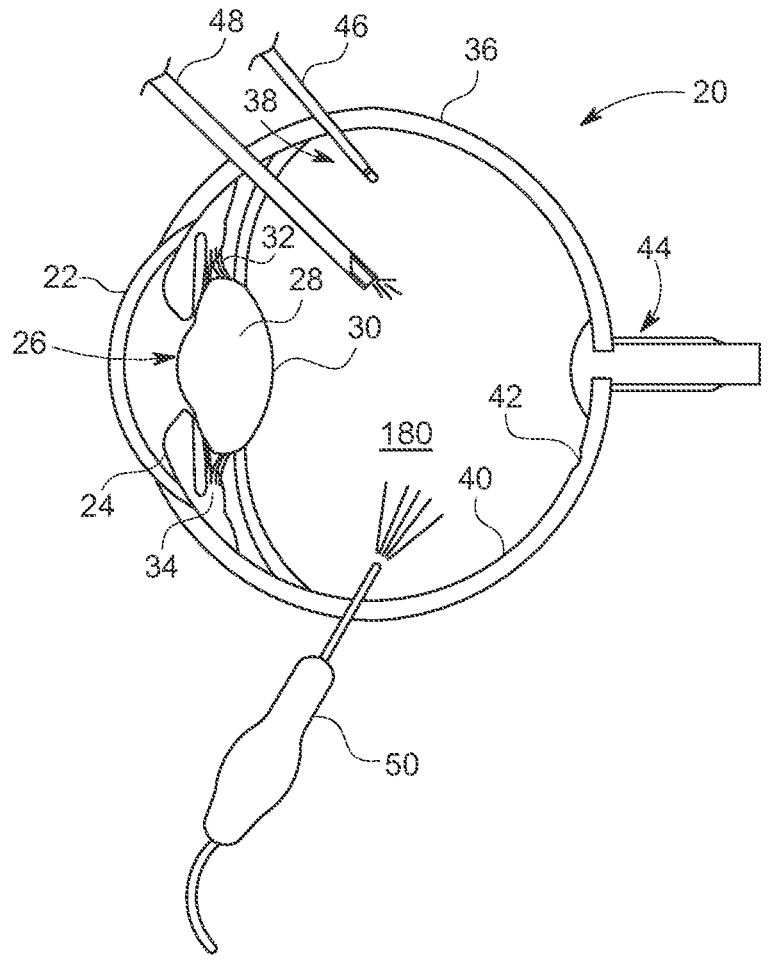
FIG. 1 is a cross-section view of an eye illustrating an internal anatomy of the eye in accordance with an embodiment.

FIG. 1 is a cross-section view of an illuminated microsurgical instrument 50 illuminating an interior region of an eye 20 in accordance with an embodiment. Various microsurgical instruments 50 may be inserted into the eye 20 to perform various surgeries. For example, a microsurgical instrument 50 may be inserted through sclera 36 (generally at the pars plana) into vitreous region 38 in connection with performing a vitreo-retinal procedure. These may include, but are not limited to, a vitrectomy probe, an infusion cannula, and an illuminated microsurgical instrument or probe for illuminating an interior of the eye 20. The microsurgical instrument 50 may include a fiber optic cable for transferring light from a light source to illuminate the inside of vitreous region 38 of eye 20 during various intra-operative procedures, such as vitreo-retinal surgery.

Figure 2A:
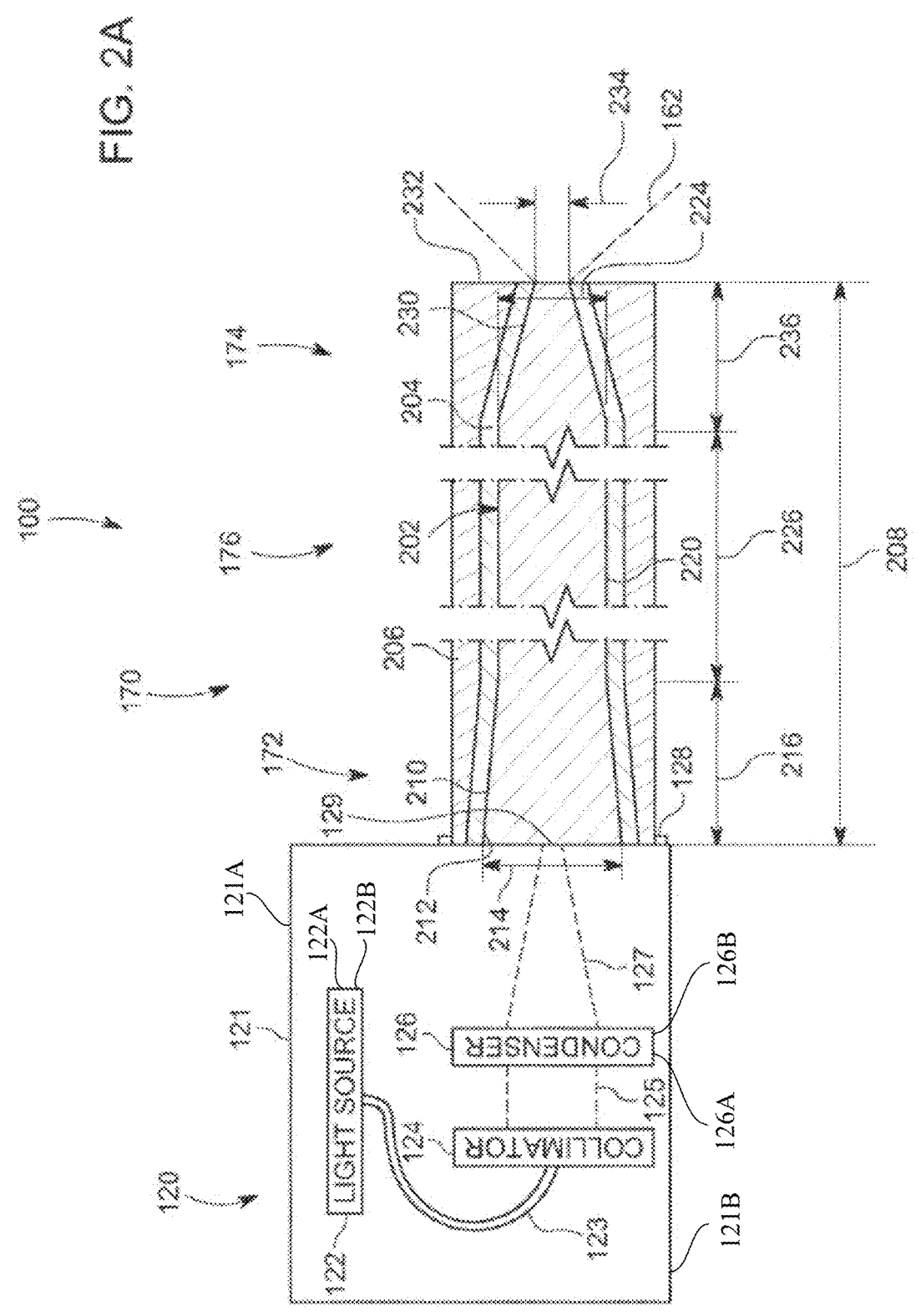
FIG. 2A is a diagram illustrating a portion of an ophthalmic illumination system, including an optical fiber.
Figure 2B:
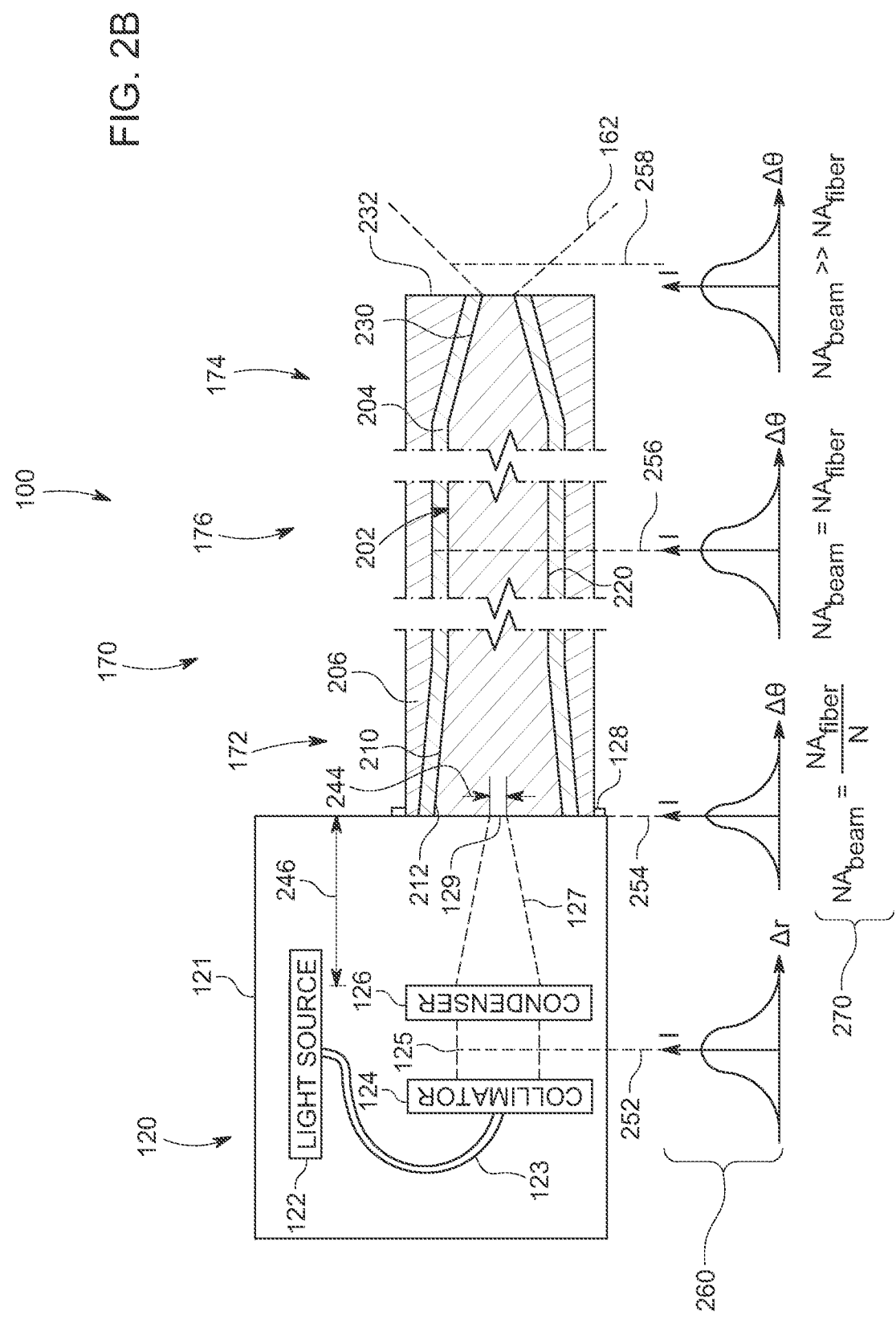
FIG. 2B is a diagram illustrating a portion of an ophthalmic illumination system, including an optical fiber.
Figure 2C:
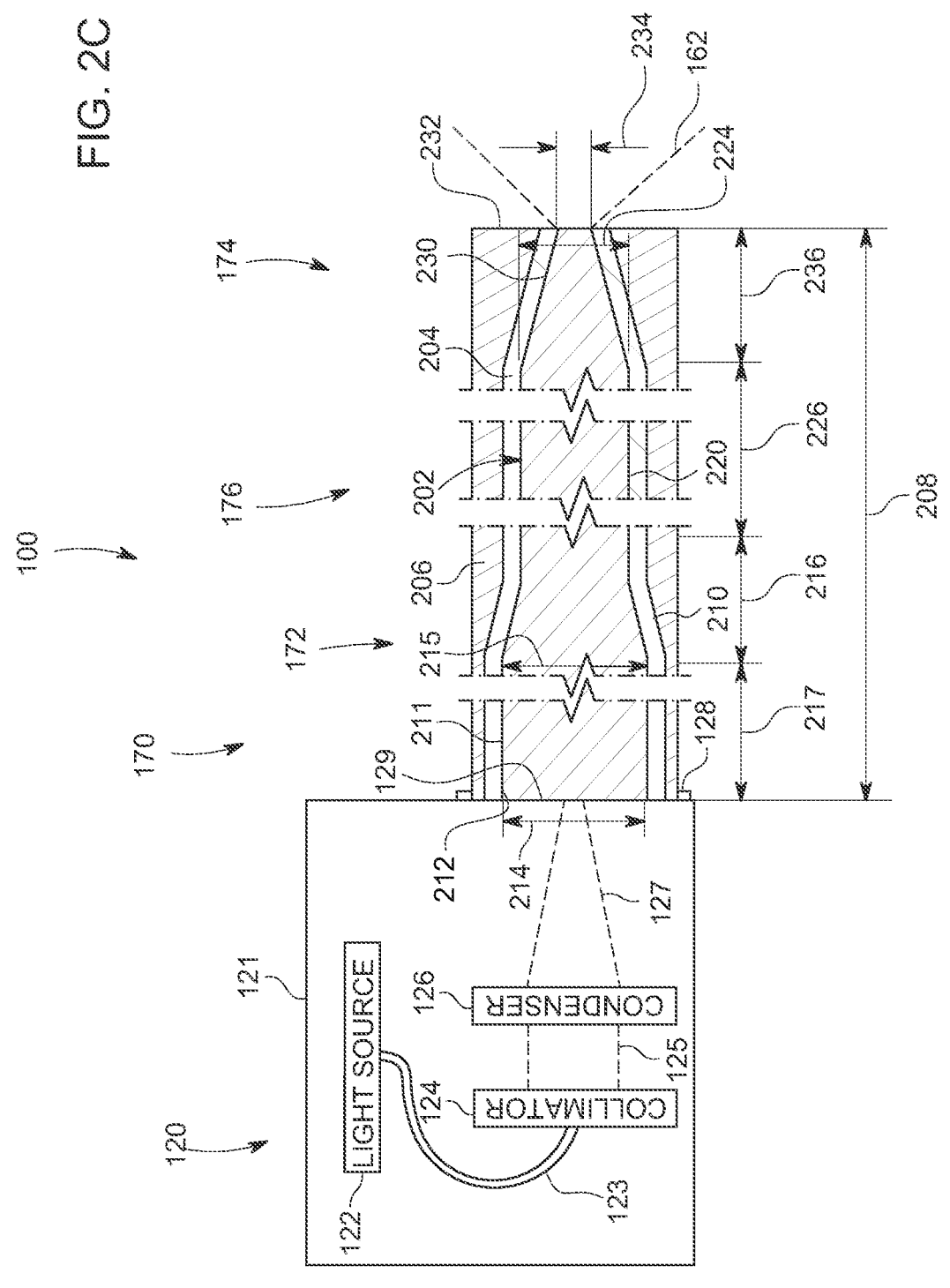
FIG. 2C is a diagram illustrating a portion of an ophthalmic illumination system, including an optical fiber.

FIGS. 2A-2C illustrate a diagram of an ophthalmic illumination system 100. The ophthalmic illumination system 100 includes a light source 122 for transmitting a light beam through an optical fiber 170 to illuminate a surgical field. The optical fiber 170 has a proximal portion 172 defining a first numerical aperture, a distal portion 174 defining a second numerical aperture, and a central portion 176 extending between the proximal portion and the distal portion 174. The optical fiber 170 is configured to receive the light beam at the proximal portion 172 at the first numerical aperture and output the light beam from the distal portion 174 at the second numerical aperture. In this way, the ophthalmic illumination system 100 provides an optical fiber 170 that emits the light beam from the light source 122 to the surgical field in an expanded light pattern relative to the originally emitted light pattern from the light source 122.

In the embodiment of FIGS. 2A-2C, the second numerical aperture is greater than the first numerical aperture. For example, the first numerical aperture of the proximal portion 172 may define a numerical aperture of about 0.5 or less, and the second numerical aperture of the distal portion 174 defines a numerical aperture of about 0.6 or greater. In addition, the third numerical aperture of the central portion 176 may define a numerical aperture of about 0.5 or less.

The light beam originating from the light source 122 can be characterized by its angular spread or divergence at various locations within the optical path between the light source 122 and the surgical field 180 (FIG. 1). A metric of the angular spread can be the numerical aperture ("NA"). Formally, NA-sin (cone half angle). The light beam within the ophthalmic illumination system 100 can thus be characterized by the numerical aperture NAbeam. With reference to FIG. 2B, mathematical descriptions 270 (FIG. 2B), discussed in greater detail below, describe NAbeam at various locations within the ophthalmic illumination system 100. The optical fiber 170 can also be characterized by an angular spread or numerical aperture NAfiber that describes the angles of light that can be accepted and transmitted by the optical fiber 170. The NAfiber can be a fixed characteristic for a given optical fiber 170. Different fibers can have different NAs. The optical fiber 170 can have any suitable numerical aperture NAfiber, including an NAfiber between approximately 0.1 and approximately 0.9, between approximately 0.1 and approximately 0.8, between approximately 0.1 and approximately 0.7, including values such as 0.12, 0.22, 0.26, 0.30, 0.37, 0.44, 0.48, 0.50, 0.63, 0.66, and/or other suitable values both larger and smaller. The NAfiber can be selected such that the optical fiber 170 transmits light with the desired angular spread. When the light beam has a numerical aperture NAbeam less than or equal to the numerical aperture NAfiber, the light beam can be transmitted by the optical fiber 170 with little to no optical losses. With reference to FIG. 2B, when the light beam has a numerical aperture NAbeam within the optical fiber 170 greater than the numerical aperture NAfiber, a portion (e.g., the higher angle rays) of the light beam can be lost in the cladding 204. Another portion (e.g., the smaller angle rays) of the light beam that has a numerical aperture NAbeam less than or equal to the numerical aperture NAfiber can transmitted by the optical fiber 170. In that regard, NAbeam within the optical path between the light source 122 and the surgical field 180 can be related to the NAfiber. The light beam at various points within the ophthalmic illumination system 100 can also be characterized by a beam diameter. Generally, within the optical fiber 170, the beam diameter of the light beam can be equal to the diameter of the optical fiber. The beam diameter and the numerical aperture NAbeam can be chosen to fill the optical fiber 170 with light for efficient transmission to the surgical field 180.

The optical fiber 170 can include a proximal portion 172 configured to receive the light beam focused by the light source 120, a distal portion 174 configured to emit the light beam within the surgical field 180, and a central portion 176 extending between the proximal portion 172 and the distal portion 174. A core diameter of the proximal portion 172 can be larger than a core diameter of the central portion 176 and a core diameter of the distal portion 174. The ophthalmic illumination system 100 can also include the surgical instrument 160 configured to be positioned within the surgical field 180. The optical fiber 170 can be coupled to the surgical instrument 160.

The ophthalmic illumination system 100 can be used during various ophthalmic surgical procedures within the surgical field 180, such as the patient's eye. Exemplary ophthalmic surgical procedures can include a diagnostic procedure, a therapeutic procedure, an anterior segment procedure, a posterior segment procedure, a vitreoretinal procedure, a vitrectomy procedure, a cataract procedure, and/or other suitable procedures. The surgical field 180 can include any suitable physiology of the patient's eye, including an anterior segment, a posterior segment, a cornea, a lens, a vitreous chamber, a retina, and/or a macula.

The surgeon can view the surgical field 180 when illuminated by light from the light source 122. The light source 122 can be any suitable light source operable to output a light beam optically coupled into the optical fiber 170, as discussed herein. For example, the light source can include a laser source, such as a supercontinuum laser source, an incandescent light bulb, a halogen light bulb, a metal halide light bulb, a xenon light bulb, a mercury vapor light bulb, a light-emitting diode (LED), other suitable sources, and/or combinations thereof. The light source 122 can output a diagnostic light beam, a treatment light beam, and/or an illumination light beam. The light beam can include any suitable wavelength(s) of light, such as visible light, infrared light, ultraviolet (UV) light, etc. For example, the light beam can transmit bright, broadband, and/or white light to illuminate the surgical field 180.

In an alternate embodiment, the light source 122 includes an array of three laser diodes that are arranged to combine and emit a single light beam that can be modulated to produce a predetermined spectral range. Each of the laser diodes may include a discrete spectral range, such as a generally blue spectral range, a generally green spectral range, and a generally red spectral range. In one embodiment, the generally blue spectral range may include a wavelength of about 440 nm to about 460 nm, the generally green spectral range may include a wavelength of about 510 nm to about 530 nm, and the generally red spectral range may include a wavelength of about 650 nm to about 670 nm. The generally blue spectral range should have a wavelength that is within a safe region of the aphakic hazard level. Although the embodiment includes three laser diodes, fewer or more laser diodes may be used.

The alternate embodiment of the ophthalmic illumination system 100 may include a plurality of controls 121A, 121B operatively connected to respective laser diodes. The controls 121A, 121B can be independently adjusted by the user to modulate the spectral ranges of each laser diode. The ophthalmic illumination system 100 includes a visual indicator that displays the color of the selected spectral range of the final light beam emitted from the system 100. This allows the user to preview the color or spectral range prior to use in a patients eye. In another alternate embodiment, the controls may include presets that allow the user to select a predetermined color or spectral range.

The light source 122 may include a despeckling mechanism 122A, e.g., a vibratory despeckling mechanism 122B, that vibrates an optical fiber portion to reduce the speckling of the combined light beam and produce more uniform illumination. A light beam produced by combining multiple individual light beams to produce a single light beam having the spectral ranges of the individual light beams, such as implemented with light source 122, may be subject to a phenomenon referred to as speckling. Speckling occurs when multiple light waves having different phases interfere with one another. When added together, the interferences produce a light wave having an intensity that varies randomly. In alternate embodiments, options for reducing speckling include, for example, using rotating diffusers or lenses arranged in the optical path of light beam 64 to disrupt the spatial coherence of the emitted laser light.

When employing laser diodes, the emitted light beam generally possesses a high degree of spatial coherence. High spatial coherence typically enables the beam to be focused to small spot sizes for delivery to fiber optic cabling. The ability to focus light emitted from laser diodes to small spot sizes may enable the use of smaller-scale optical fibers for transmitting the light emitted from the light source 122 to the interior of eye 20. Smaller-scale optical fibers generally have a diameter (or other largest cross-sectional dimension) of less than 250 microns. When integrated with a microsurgical instrument 50, the small diameter of smaller scale optical fiber may enable a reduction in the cross-sectional area of the instrument 50, which in turn may reduce the size of the surgical incision in the eye 20 (see FIG. 1) through which the probe is inserted.

The light beam can traverse an optical path extending between the light source 122 and the surgical field 180, including through the optical fiber 170. An optical fiber 123 that facilitates transmission of the light beam can be mechanically and/or optically coupled with and extend between the light source 122 and surgical instrument 160.

From the light source 122, the light beam 127 can be transmitted to the optical fiber 170 through air/free space or another optical fiber. The optical fiber 170 can be configured to transmit light from the light source 122 to the surgical field 180. In general, as illustrated in FIG. 1, the optical fiber 170 can include the proximal portion 172, the distal portion 174, and the central portion 176. The proximal portion 172 can receive the light beam 127 from the light source 122. Once received at the proximal portion 172, the light propagates distally along the optical fiber 170 towards the surgical field 180. The central portion 176 can extend and transmit light between the proximal portion 172 and the distal portion 174. The distal portion 174 can deliver emitted light 162 into the surgical field 180. At least a portion of the optical fiber 170, such as the distal portion 174, can be positioned within the surgical field 180. In that regard, the optical fiber 170 can be a disposable component configured for single use. For example, the distal portion 174 can be coupled to the surgical instrument 160 positioned within the surgical field 180. The distal portion 174 can be disposed within or coupled to an exterior of the surgical instrument 160. The central portion 176 and/or the proximal portion 172 can also be coupled to the surgical instrument 160. The surgical instrument 160 can be any suitable tool used by the surgeon during the ophthalmic surgical procedure, including a spot illuminator, a chandelier illuminator, an endoilluminator, an infusion cannula, a cutting probe, a vitrectomy probe, an aspiration probe, scissors, and forceps, for example. The surgical instrument 160 can be an infusion device 132 or a probe 152, described in greater detail below. In alternate embodiments, the ophthalmic illumination system 100 may include other components, such as a condenser 126 having a plurality of lenses 126A, 126B. The condenser 126 can be configured to focus the light beam outputted by the light source 122. In an alternate embodiment, the light source 122 can be part of an illumination subsystem 120. The optical fiber 170 can be in optical communication with the illumination subsystem 120. The illumination subsystem 120 can include all or a portion of the optical components associated with delivering light to the surgical field 180. The illumination subsystem 120 can include various other optical components, such as mirrors, including hot or cold dichroic mirrors and fold mirrors, beam splitters, lenses, gratings, filters, and/or combinations thereof, which facilitate transmission of light to the surgical field 180. The light source 122, the collimator 124, and the condenser 126 can be disposed within a housing 121 of the illumination subsystem 120. The housing 121 can be any suitable enclosure that maintains the light source 122, the collimator 124, and the condenser 126 in a fixed arrangement relative to one another.

Portions of the ophthalmic illumination system 100, including the optical fiber 170, are illustrated in FIGS. 2A, 2B, and 2C. FIGS. 2A, 2B, and 2C can illustrate a cross-sectional view of the optical fiber 170. The optical fiber 170 can include a core 202, cladding 204, and a coating 206. The core 202 can be a cylinder of glass, plastic, silica, borosilicate, and/or other suitable material through which light propagates. The cladding 204 can surround the core 202 and confine the light within the core 202. The cladding 204 can include a dielectric material with an index of refraction less than the index of refraction of the core 202. The coating 206 can surround the cladding 204 and protect the optical fiber 170 from physical damage.

The light source 120 can direct the light beam 127 onto the proximal portion 172 of the optical fiber 170. The core 202 within the proximal portion 172 of the optical fiber 170 can include a tapered section 210. For example, the light source 120 can direct the light beam 127 onto the tapered section 210, as illustrated in FIGS. 2A and 2B. In that regard, the diameter and the cross-sectional area of the core 202 within the tapered section 210 can decrease distally along the optical fiber 170. The core 202 can include a first or entrance aperture 212 located at the proximal-most end of the optical fiber 170. The entrance aperture 212 can be a part of the core 220. For example, the entrance aperture 212 can be a proximal face of the core 202 that interfaces with the light beam 127. The entrance aperture 212 can be a part of the tapered section 210. The entrance aperture 212 can have a diameter 214, illustrated in FIGS. 2A and 2C. The diameter 214 of the entrance aperture 212 and/or the diameter 215 of a section 211 can be the largest diameter of the core 202 along a length 208 of the optical fiber 170. The light beam 127 can be optically coupled into the optical fiber 170 at the entrance aperture 212. For example, the beam spot 129 can ideally be centered within the entrance aperture 212. The tapered section 210 can be similar to a funnel with an enlarged diameter to receive the light beam 127.

Alternatively, as illustrated in FIG. 2C, the core 202 within the proximal portion 172 of the optical fiber 170 can include a section 211 having a constant size and shape. For example, the section 211 can be a straight, non-tapered section. The light source 120 can direct the light beam 127 onto the section 211. The section 211 can be positioned proximally of the tapered section 210. The entrance aperture 212 can be a part of the section 211. The section 211 can have a diameter 215 and a length 217. The diameter 215 of the section 211 can be substantially equal to the diameter 214 of the entrance aperture 212. The diameter 215 and the cross-sectional area of the section 211 can remain constant along the length 217 of the optical fiber 170. The length 217 can be related to the diameter 215 by a mathematical relationship. For example, the ratio of the length 217 and the diameter 215 can be greater than one thousand. When the length 217 and the diameter 215 satisfy this relationship, the light within the optical fiber 170 can laterally spread out as the light laterally fills the core 202. Thus, the light can become spatially homogenized within the section 211, before the light encounters the tapered region 210.

The core 202 within the central portion 176 of the optical fiber 170 can include a section 220 having a constant size and shape. For example, the section 220 can be a straight, non-tapered section. The section 220 can have a diameter 224. The diameter 224 and the cross-sectional area of the section 220 can remain constant along the central portion 176 of the optical fiber 170.

The core 202 within the distal portion 174 of the optical fiber 170 can include a tapered section 230. In that regard, the diameter and the cross-sectional area of the core 202 within the tapered section 230 can decrease distally along the optical fiber 170. The tapered section 230 can terminate at a tip 232 at the distal-most end of the optical fiber 170. Emitted light 162 can be delivered into the surgical field 180 via the tip 232. The tip 232 can have a diameter 234. The tapered section 230 can include a borosilicate taper, for example. The tapered section 230 can be configured to output the emitted light 162 with a relatively large or a relatively small angular spread to illuminate the surgical field 180. The cladding 204 in the tapered section 230 can be stripped from the optical fiber 170 in some examples. The core 202 within the distal portion 174 of the optical fiber 170 can have a constant size and shape in some examples. For example, core 202 within the distal portion 174 can be a straight, non-tapered section. The core 202 within the distal portion 174 can have a diameter that increases distally along the optical fiber 170, in some examples. For example, the core 202 can be a tapered section with an increasing diameter. The core 202 within the distal portion 174 of the optical fiber 170 can include a scattering section in lieu of or in addition to the tapered section 230 in some examples. The tip 232 can be variously sized and shaped, including conically shaped, spherically shaped, and/or otherwise suitably shaped, to facilitate output of the emitted light 162 within the surgical field 180 with the desired angular spread.

The diameter of the core 202 can vary between the proximal portion 172, the central portion 176, and the distal portion 174 of the optical fiber 170. The diameter 224 within the section 220 can be generally described as dfiber. For example, the value of dfiber can be between approximately 10 μm and approximately 100 μm, between approximately 10 μm and approximately 50 μm, between approximately 20 μm and approximately 30 μm, including values such as 20 μm, 22 μm, 25 μm, 27 μm, 30 μm, and/or other suitable values, both larger and smaller. The diameter 214 of the entrance aperture 212 can be a multiple of the diameter 224 and generally described as Ndfiber. The parameter N can thus describe the larger size of the entrance aperture 212 relative to the diameter 224 of the central portion 176. The value of the parameter N can be between 1 and 10, between 1 and 5, between 2 and 4, including, values such as 2, 2.5, 3, 3.1, 3.3, 4, and/or other suitable values, both larger and smaller. The value of the parameter N can be selected to achieve improved transmission of misaligned light while advantageously preserving a relatively small diameter (e.g., the diameter 214) for the optical fiber 170. The relatively small diameter of the optical fiber 170 can allow the optical fiber 170 to be advantageously integrated in various surgical instruments (e.g., the surgical instrument 160). The diameter 215 of the section 211 (FIG. 2C) can be substantially equal to the diameter 214 of the entrance aperture 212. The diameter of the tapered section 210 within the proximal portion 172 can decrease distally from Ndfiber at the entrance aperture 212 or the section 211, to dfiber at the central portion 176. The diameter 234 of the tip 232 can be any suitable size equal to or smaller than dfiber of the diameter 224. The diameter 234 of the tip 232 can also be larger than dfiber of the diameter 224 in some examples. The value of diameter 234 of the tip 232 can be between approximately 1 μm and approximately dfiber of the diameter 224, and/or other suitable values, both larger and smaller. The diameter of the tapered section 230 within the distal portion 174 can decrease distally from dfiber at the central portion 176 to the diameter 234 at the tip 232. Thus, the diameter of the core 202 within the proximal portion 172 can be larger than the diameter of the core 202 in the central portion 176 and the distal portion 174. The diameter of the core 202 within the central portion 176 can be larger than the diameter of the core 202 in the distal portion 174.

The optical fiber 170 can have any suitable length 208. For example, the length 208 can be between approximately 0.1 m and approximately 10 m. The tapered section 210 of the proximal portion 172 can have a length 216. The length 216 can be any suitable length. For maximum transmittance of light through the tapered section 210 into the section 220, the taper can be gradual. Linear, or non-linear. For example, the shape of the tapered section 210, the angle of the taper, and/or the length 216 can be selected to provide a gradual taper. For example, the length 216 of the tapered section 210 of the proximal portion 172 can be any value that is equal to or greater than approximately one hundred times the difference between the diameter 214 and the diameter 224. For example, the diameter 224 can be 25 microns, and the diameter 214 can be 75 microns (e.g., the parameter N multiplied by the diameter 224, with N=3, or 325 μm). For maximum throughput, the length 216 can be any length longer than 5 mm (e.g., 100 (75 μm-25 μm)). The section 220 within the central portion 176, which has a constant shape, can have any suitable length 226. For example, the length 226 can between approximately 10 mm and approximately 1000 mm, between approximately 50 mm and approximately 500 mm, between approximately 100 mm and approximately 200 mm, including values such as 100 mm, 125 mm, 145 mm, 150 mm, 166 mm, 200 mm, and/or other suitable values both larger and smaller. The tapered section 230 of the distal portion 174 can have any suitable length 236. For example, the length 236 can between approximately 5 microns and approximately 1000 microns, between approximately 5 microns and 500 microns, between approximately 10 microns and 100 microns, including values such as 10 microns, 25 microns, 50 microns, 66 microns, 100 microns, and/or other suitable values both larger and smaller. The core/cladding diameter ratio can remain constant or change along the length 216 of the tapered section 210 and/or the length 236 of the tapered section 230.

A mathematical relationship can describe the angular spread and the beam diameter of the light transmitted by the optical fiber 170. For example, the product of the angular spread, such as the NAbeam, and the beam diameter can be constant. That is, the angular spread and the beam diameter can have a reciprocal relationship. Thus, as the beam diameter decreases, the angular spread increases and vice versa. For example, within the tapered region 210, as the beam diameter decreases (because the diameter of the core 202 decreases), the angular spread of the light can correspondingly increase. Similarly, within the tapered region 230, the angular spread of the light can increase as the beam diameter and the diameter of the core 202 decreases.

Figure 3A:
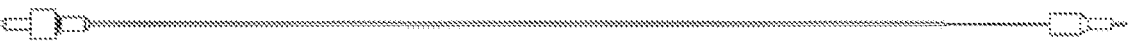
FIG. 3A is overhead view of a first alternate embodiment of the illuminated microsurgical instrument.
Figure 3B:
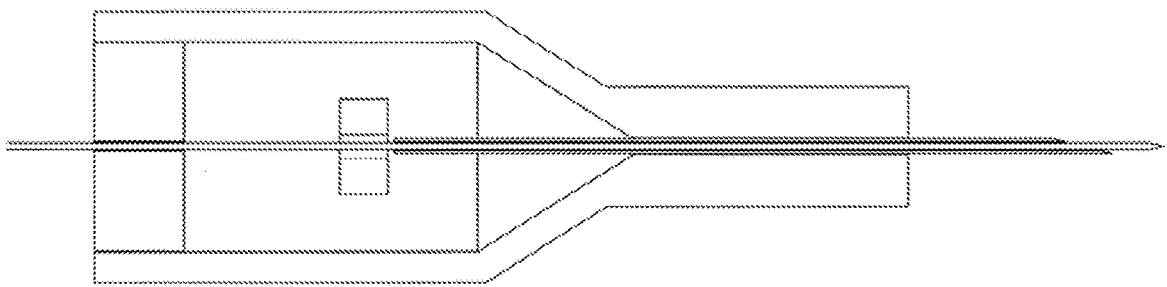
FIG. 3B is an enlarged cross-section view of the first alternate embodiment of the illuminated microsurgical instrument in an open position.
Figure 3C:
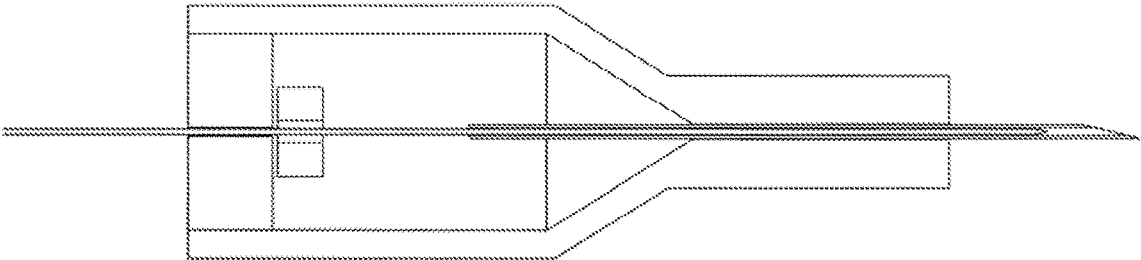
FIG. 3C is an enlarged cross-section view of the first alternate embodiment of the illuminated microsurgical instrument in a closed position.

Generally, FIGS. 3A-4D illustrate various embodiments of illuminated microsurgical instruments that may be used in conjunction with the ophthalmic illumination system 100. FIG. 3A is overhead view of a first alternate embodiment of the illuminated microsurgical instrument 50. FIG. 3B is an enlarged cross-section view of the first alternate embodiment of the illuminated microsurgical instrument in an open position. FIG. 3C is an enlarged cross-section view of the first alternate embodiment of the illuminated microsurgical instrument in a closed position. The first alternate embodiment of the illuminated instrument may be referred to as a micro chandelier. The micro chandelier is small enough to not need any suturing when removing from the eye. This allows the surgeon to easily move the chandelier to any location needed during surgery-we believe this feature is novel and is not elsewhere on the market. The chandelier consists of a needle/cannula hub that can be sized to be held with the finger or with a pair of needle holders/blunt forceps. The needle of the chandelier is beveled and sharp to pierce the sclera as well as act as a shield to block glare. The fiber is fixed inside of the needle/cannula hub via a fiber stop and a plug on the back-side of the cannula/needle hub. The fiber stop facilitates adjustability of the fiber tip with respect to the tip of the needle. The fiber stop provides a limit to this adjustability by contact with the backside of the needle and the plug in the cannula/needle hub. The chandelier is inserted into the eye first by recessing the fiber into the needle until the stop is contacting the plug. The cannula hub is then inserted into the eye into the position the surgeon desires via his fingers or a pair of needle holders. The fiber is then adjusted to the position desired by the surgeon. If the surgeon wishes to move the chandelier during the case, they first recess the fiber into the needle and then remove the cannula hub from the eye. The surgeon is then able to reinsert the chandelier wherever they chose to.

Figure 4A:
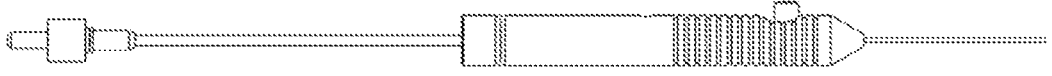
FIG. 4A is an overhead view of a second alternate embodiment of the illuminated microsurgical instrument.
Figure 4B:
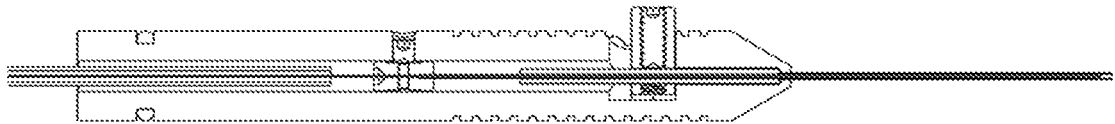
FIG. 4B is cross-section view of a second alternate embodiment of the illuminated microsurgical instrument in a closed position.
Figure 4C:
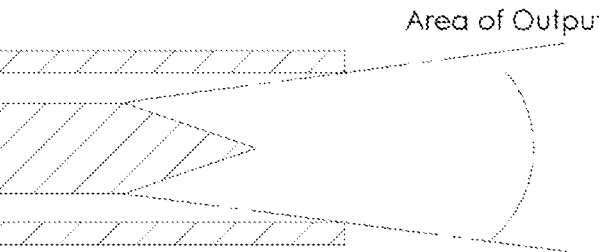
FIG. 4C is an enlarged view of a second alternate embodiment of the illuminated microsurgical instrument with a non-beveled tip in a closed position.
Figure 4D:
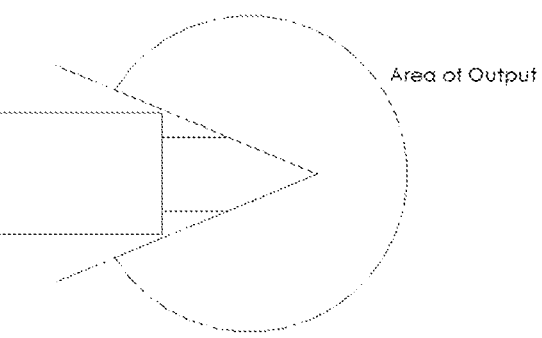
FIG. 4D is an enlarged view of a second alternate embodiment of the illuminated microsurgical instrument with a non-beveled tip in an open position.
Figure 4E:
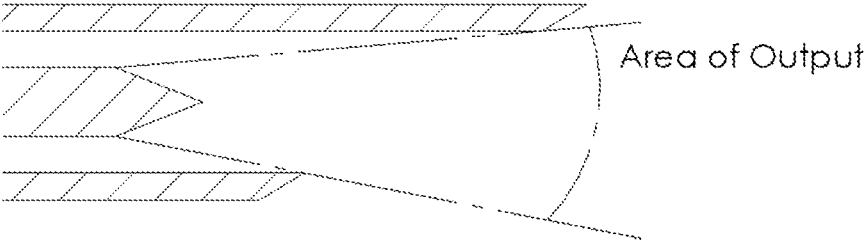
FIG. 4E is an enlarged view of a second alternate embodiment of the illuminated microsurgical instrument with a beveled tip in a closed position.
Figure 4F:
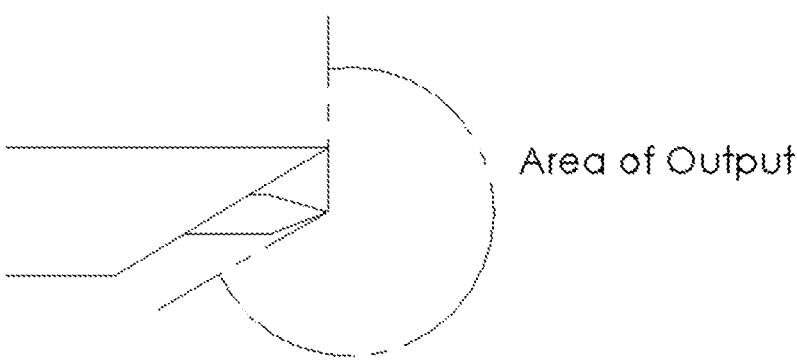
FIG. 4F is an enlarged view of a second alternate embodiment of the illuminated microsurgical instrument with a beveled tip in an open position.

FIG. 4A is an overhead view of a second alternate embodiment of the illuminated microsurgical instrument 50. FIG. 4B is cross-section view of a second alternate embodiment of the illuminated microsurgical instrument in a closed position. FIG. 4C is an enlarged view of a second alternate embodiment of the illuminated microsurgical instrument with a non-beveled tip in a closed position. FIG. 4D is an enlarged view of a second alternate embodiment of the illuminated microsurgical instrument with a non-beveled tip in an open position. FIG. 4E is an enlarged view of a second alternate embodiment of the illuminated microsurgical instrument with a beveled tip in a closed position. FIG. 4F is an enlarged view of a second alternate embodiment of the illuminated microsurgical instrument with a beveled tip in an open position. The second alternate embodiment of the illuminated microsurgical instrument may be referred to as an adjustable light pipe. A light pipe that combines the advantages of a widefield as well as a focal light pipe-we believe this feature is novel and is not elsewhere on the market. The probe consists of a button that is attached to the piston tube. A coned fiber is fixed in place relative to the handle via a fiber couple and a set screw in the handle. The button is able to be actuated which in turn actuates the piston tube in position with respect to the tip of the fiber. The button actuated to the very front is the "closed position". This position recesses the fiber into the piston tube. The button actuated to the very rear is the "open position". This position protrudes the fiber from the piston tube. In the open position, the light pipe is comparable to a widefield light pipe. The output of the fiber can be compared to a room light or a "chandelier." In the closed position, the light pipe is comparable to a focal light pipe. The output of the fiber can be compared to a flashlight with a focused/narrow beam of light. The focal beam is more "narrow" compared to a regular focal light pipe. That is, the beam of light is more focused and facilitates use across the eye whereas a normal focal light pipe is unable to do this. The probe is able to be actuated continuously from the "open" position to the "closed" position. This allows the surgeon to decide how wide the output of light needs to be during use rather than being restricted to a single angle of output. The fiber is fixed to the back of the fiber couple, the fiber couple is therefore vented to facilitate venting of air when being inserted into the eye. This combats air bubbles being released into the eye during surgery which obstructs the view of the surgeon. The probe can be provided with a beveled tip, which acts like a shield. The shield is positioned between the surgeon and the inside of the eye, which cuts down on glare when being used.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

The invention claimed is:

1. An illumination system, comprising:
   a light source having an array of laser diodes configured to emit a combined light beam;
   a despeckling mechanism to reduce speckling in the light beam;
   an optical fiber receiving and transmitting the light beam, the optical fiber including a proximal portion configured to receive the light beam from the light source, the proximal portion having a first numerical aperture, the optical fiber including a distal portion configured to emit the light beam to illuminate a surgical field, the distal portion having a second numerical aperture, and the optical fiber including a central portion extending between the proximal portion and the distal portion, the central portion having a third numerical aperture, wherein the optical fiber is configured to receive the light beam at the proximal portion at the first numerical aperture and output the light beam from the distal portion at the second numerical aperture, and a micro chandelier, the micro chandelier including a needle and a cannula hub, the cannula hub being positioned at a back side of the micro chandelier, the needle being positioned opposite the cannula hub, wherein the optical fiber is attached inside and traverses through the micro chandelier, the optical fiber extending through the cannula hub and the needle, the optical fiber being movably attached to the cannula hub such that a tip of the distal portion of the optical fiber moves in and out of the needle, wherein the optical fiber includes a fiber stop, the fiber stop being positioned inside the micro chandelier and between the cannula hub and the needle of the micro chandelier, and the fiber stop being configured to move between the cannula hub and the needle, and wherein the cannula hub has a first plug facing the needle and the needle has a second plug facing the cannula hub, the fiber stop being configured to fit into the first plug thereby fixing the optical fiber on the micro chandelier with the tip of the optical fiber being recessed inside the needle, and the fiber stop being further configured to fit into the second plug thereby fixing the optical fiber on the micro chandelier with the tip of the optical fiber being extended out of the needle.

2. The illumination system of claim 1, wherein the second numerical aperture is greater than the first numerical aperture.

3. The illumination system of claim 1, wherein the proximal portion of the optical fiber has a numerical aperture of about 0.5 or less.

4. The illumination system of claim 1, wherein the distal portion of the optical fiber has a numerical aperture of about 0.6 or greater.

5. The illumination system of claim 1, wherein the central portion of the optical fiber has a numerical aperture of about 0.5 or less.

6. The illumination system of claim 1, wherein the light source emits a light beam having a numerical aperture of about 0.5 or less.

7. The illumination system of claim 1, wherein the proximal portion further comprises a first tapered section with a first proximal end and a first terminal end.

8. The illumination system of claim 1, wherein the distal portion further comprises a second tapered section with a second proximal end and a second terminal end.

9. The illumination system of claim 1, wherein the central portion includes a core diameter having a constant diameter over length of the central portion.

10. The illumination system of claim 1, wherein the array of laser diodes includes a red laser diode, a green laser diode, and a blue laser diode.

11. The illumination system of claim 10, wherein the red laser diode operates in a spectral range having a wavelength of between 650 nm to 670 nm, the green laser diode operates in a spectral range having a wavelength of between 510 nm to 530 nm, and the blue laser diode operates in a spectral range having a wavelength of between 440 nm to 460 nm.

12. The illumination system of claim 1, wherein the combined light beam emitted from the array of laser diodes is modulated to produce a predetermined spectral range.

13. The illumination system of claim 1, wherein the light source includes at least one control element configured to be adjusted to control the spectral range of the combined light beam.

14. The illumination system of claim 1, wherein the light source includes control elements associated with each of the laser diodes to independently control output from each of the laser diodes to control the spectral output of the combined light beam.

15. The illumination system of claim 1, wherein the despeckling mechanism is a vibratory despeckling mechanism configured to physically vibrate at least one of the optical fiber and the array of laser diodes.

16. The illumination system of claim 1, wherein a source optical fiber extends between the laser diodes and the optical fiber to transmit the combined light beam to the optical fiber, the despeckling mechanism operably coupled to the source optical fiber to reduce speckling in the light beam transmitted through the source optical fiber.

17. The illumination system of claim 16, wherein the despeckling mechanism is a vibratory despeckling mechanism configured to vibrate the source optical fiber.

18. The illumination system of claim 1, wherein the despeckling mechanism includes lenses arranged in the optical path of the light beam to disrupt the spatial coherence of the emitted light beam.

*    *    *    *    *